(12) United States Patent
Warren

(10) Patent No.: US 8,980,225 B2
(45) Date of Patent: Mar. 17, 2015

(54) MAGNETIC RESONANCE IMAGING AND/OR SPECTROSCOPY CONTRAST AGENTS AND METHODS OF USE THEREOF

(75) Inventor: Warren S. Warren, Durham, NC (US)

(73) Assignee: Duke University, Durham, NC (US)

(*) Notice: Subject to any disclaimer, the term of this patent is extended or adjusted under 35 U.S.C. 154(b) by 587 days.

(21) Appl. No.: 13/056,795

(22) PCT Filed: Jul. 31, 2009

(86) PCT No.: PCT/US2009/052393
§ 371 (c)(1),
(2), (4) Date: Apr. 25, 2011

(87) PCT Pub. No.: WO2010/014893
PCT Pub. Date: Feb. 4, 2010

(65) Prior Publication Data
US 2011/0195028 A1    Aug. 11, 2011

Related U.S. Application Data

(60) Provisional application No. 61/085,178, filed on Jul. 31, 2008.

(51) Int. Cl.
*A61B 5/055* (2006.01)
*A61B 5/05* (2006.01)
*G01R 33/28* (2006.01)
*G01R 33/56* (2006.01)

(52) U.S. Cl.
CPC .......... *G01R 33/282* (2013.01); *G01R 33/5601* (2013.01); *G01R 33/5605* (2013.01)
USPC ............................................ 424/9.3; 600/420

(58) Field of Classification Search
CPC ..................... G01R 33/56051; G01R 33/5605; G01R 33/282
USPC ............................................ 424/9.3; 600/420
See application file for complete search history.

(56) References Cited

U.S. PATENT DOCUMENTS

| 7,474,095 B2 | 1/2009 | Levitt et al. |
|---|---|---|
| 2007/0063700 A1 | 3/2007 | Levitt et al. |
| 2008/0260649 A1* | 10/2008 | Thaning et al. ............... 424/9.36 |

FOREIGN PATENT DOCUMENTS

| WO | WO2005/015253 | 2/2005 |
|---|---|---|
| WO | WO2010/014893 | 2/2010 |

OTHER PUBLICATIONS

Abragam, A., and Goldman, M., "Principles of dynamic nuclear polarisation," Rep. Prog. Phys. vol. 41 pp. 395-467 (1978).
Abraham, R.J., and Bernstein, H.J., "The Analysis of Nuclear Magnetic Resonance Spectra v. The Analysis of Deceptively Simple Spectra," Canadian Journal of Chemistry. vol. 39 pp. 216-230 (1961).
Ahuja et al., "Molecular properties determined from the relaxation of long-lived spin states," The Journal of Chemical Physics. vol. 127 pp. 134112-1-134112-6 (2007).
Anet, "Some Aspects of the Nuclear Magnetic Resonance Spectra of Compounds Containing C-Methyl Groups," Canadian Journal of Chemistry. vol. 39 pp. 2262-2273 (1961).
Ardenkjaer-Larsen et al., "Increase in signal-to-noise ratio of >10,000 times in liquid-state NMR," PNAS. vol. 100, No. 18 pp. 10158-10163 (2003).
Bajaj et al., "Dynamic nuclear polarization at 9T using a novel 250 GHz gyrotron microwave source," Journal of Magnetic Resonance vol. 160 pp. 85-90 (2003).
Becker, High Resolution NMR: Theory and Chemical Applications. Chapter 6. Academic, San Diego, CA pp. 171-175 (2000).
Bell, "The Reversible Hydration of Carbonyl Compounds," Adv. Phys. Org. Chem. vol. 4 pp. 1-29 (1966).
Bell, R.P., and McDougall, A.O., "Hydration Equilibria of Some Aldehydes and Ketones," Trans. Faraday Soc. vol. 56 pp. 1281-1285 (1960).
Bhattacharya et al., "Communication: Towards hyperpolarized $^{13}$C-succinate imaging of brain cancer," Journal of Magnetic Resonance. vol. 186 pp. 150-155 (2007).
Bowers, C.R., and Weitekamp, D.P., "Transformations of Symmetrization Order to Nuclear-Spin Magnetization by Chemical Reaction and Nuclear Magnetic Resonance," Physical Review Letters. vol. 57, No. 21 pp. 2645-2648 (1986).
Bowers, C.R., and Weitkamp, D.P., " Parahydrogen and Synthesis Allow Dramatically Enhanced Nuclear Alignment," Journal American Chemical Society. vol. 109 pp. 5541-5542 (1987).
Carravetta et al., "Beyond the $T_1$ Limit: Singlet Nuclear Spin States in Low Magnetic Fields," Physical Review Letters. vol. 92, No. 15 pp. 153003-1-153003-4 (2004).
Carravetta M. and Levitt M.H., "Long-Lived Nuclear Spin States in High-Field Solution NMR," Journal American Chemical Society. vol. 126 pp. 6228-6229 (2004).
Carravetta M. and Levitt M.H., "Theory of long-lived nuclear spin states in solution nuclear magnetic resonance. I. Singlet states in low magnetic field," The Journal of Chemical Physics. vol. 122 pp. 214505-1-214505-14 (2005).
Chekmenev et al., "Pasadena Hyperpolarization of Succinic Acid fro MRI and NMR Spectroscopy," JACS. vol. 130 pp. 4212-4213 (2008).
Day et al., "Co-acquisition of hyperpolarised $^{13}$C and $^{15}$N NMR spectra," Magnetic Resonance in Chemistry. vol. 45 pp. 1018-1021 (2007).

(Continued)

*Primary Examiner* — Michael G Hartley
*Assistant Examiner* — Leah Schlientz
(74) *Attorney, Agent, or Firm* — Jenkins, Wilson, Taylor & Hunt, P.A.

(57) ABSTRACT

The presently disclosed subject matter demonstrates that a spin state which has zero magnetic resonance signal, but an extremely long lifetime, can be used to store magnetization, which can then be recovered into an observable transition. Coupled with hyperpolarization techniques, this permits the preparation of a wide range of contrast agent molecules for use in magnetic resonance imaging (MRI) techniques that have long effective relaxation time.

42 Claims, 4 Drawing Sheets

(56) References Cited

OTHER PUBLICATIONS deBoer et al., "Dynamic Polarization of Protons, Deuterons, and Carbon-13 Nuclei: Thermal Contact Between Nuclear Spins and an Electron Spin-Spin Interaction Reservoir," Journal of Low Temperature Physics. vol. 15, Nos. 3/4 pp. 249-267 (1974).

de Boer, W., and Niinikoski T., "Dynamic Proton Polarization in Propanediol Below 0.5 K," Nuclear Instruments and Methods. vol. 114 pp. 495-498 (1974).

Duckett, S.B., and Sleigh, C.J., "Applications of the parahydrogen phenomenon: A chemical perspective," Progress in Nuclear Magnetic Resonance Spectroscopy. vol. 34, No. 1 pp. 71-92 (1999).

Gabellieri et al., "Therapeutic Target Metabolism Observed Using Hyperpolarized $^{15}N$ Choline", Journal of American Chemical Society. vol. 130 pp. 4598-4599 (2008).

Golman et al., "Parahydrogen-Induced Polarization in Imaging: Subsecond $^{13}C$ Angiography," Magnetic Resonance in Medicine. vol. 46 pp. 1-5 (2001).

Golman et al., "Molecular imaging with endogenous substances," PNAS. vol. 100, No. 18 pp. 10435-10439 (2003).

Golman et al., "Metobolic Imaging by Hyperpolarized $^{13}C$ Magnetic Resonance Imaging for In vivo Tumor diagnosis," Cancer Research. vol. 66, No. 22 pp. 10855-10860 (2006).

Greenzaid et al., "A Nuclear Magnetic Resonance Study of the Reversible Hydration of Aliphatic Aldehydes and Ketones. I. Oxygen-17 and Proton Spectra and Equilibrium Constants," Journal of the American Chemical Society. vol. 89, No. 4 pp. 749-756 (1967).

Hall et al, "Polarization-Enhanced NMR Spectroscopy of Biomolecules in Frozen Solution," Science. vol. 276 pp. 930-932 (1997).

Hoecker, W.H., and Hammer, B.W., "Distribution of Diacetyl and Acetylmethylcarbinol Between Fat and Water, With Special Reference to Butter," J. Dairy Sci. vol. 25 pp. 175- 185 (1942).

Jakobsen et al., "Salety of ultrasound contrast agents," Eur. Radiol. vol. 15 pp. 941-945 (2005).

Johansson et al., "Cerebral Perfusion Assessment by Bolus Tracking Using Hyperpolarized $^{13}C$," Magnetic Resonance in Medicine. vol. 51 pp. 464-472 (2004).

Kiselyov et al., "4-(Azolylphenyl)-phthalazin-1-amines: Novel Inhibitors of VEGF Receptors I and II," Chemical Biol. Drug Des. vol. 68 pp. 308-313 (2006).

Kurhanewicz et al., "Current and Potential Applications of Clinical $^{13}C$ MR Spectroscopy," The Journal of Nuclear Medicine. vol. 49, No. 3 pp. 341-344 (2008).

MacFall et al., "Human Lung Air Spaces: Potential for MR Imaging with Hyperpolarized He-3," Radiology. vol. 200, No. 2 pp. 553-558 (1996).

McCarney et al., "Hyperpolarized water as an authentic magnetic resonance imaging contrast agent," PNAS. vol. 104, No. 6 pp. 1754-1759 (2007).

McConnel et al., "Analysis of Spin-Spin Multiplets in Nuclear Magnetic Resonance Spectra," The Journal of Chemical Physics. vol. 23, No. 6 pp. 1152-1159 (1955).

Merritt et al., "Hyperpolarized $^{13}C$ allows a direct measure of flux through a single enzyme-catalyzed step by NMR," PNAS. vol. 104, No. 50 pp. 19773-19777 (2007).

Musher, J.I., and Corey, E.J., "Virtual Long-Range Spin-Spin Couplings in NMR," Tetrahedron. vol. 18 pp. 791-809 (1962).

Natterer, J. and Bargon, J., "Parahydrogen induced polarization," Progress in Nuclear Magnetic Resonance Spectroscopy. vol. 31 pp. 293-315 (1997).

Notification Concerning Transmittal of the International Preliminary Report on Patentability (Chapter I of the Patent Cooperation Treaty) corresponding to International Patent Application No. PCT/US2009/052393 dated Feb. 10, 2011.

Notification of Transmittal of the International Search Report and the Written Opinion of the International Searching Authority, or the Declaration corresponding to International Patent Application No. PCT/US2009/052393 dated Apr. 23, 2010.

Olesen, O.V., and Linnet, K., "Hydroxylation and Demethylation of the Tricyclic Antidepressant Nortiptyline by cDNA-Expressed Human Cytochrome P-450 Isozymes," Drug Metabolism and Disposition. vol. 25, No. 6 pp. 740-744 (1997).

Pileio et al., "J-Stabilization of singlet states in the solution NMR of multiple-spin systems," Journal of Magnetic Resonance. vol. 187, No. 1 pp. 141-145 (2007).

Pople et al., "The Anaysis of Nuclear Magnetic Resonance Spectra. II. Two Pairs of Two Equivalent Nuclei," Canadian Journal of Chemistry. vol. 35 pp. 1060-1072 (1957).

Salerno et al., "Hyperpolarized noble gas MR imaging of the lung: Potential applications," European Journal of Radiology. vol. 40 pp. 33-44 (2001).

van Rooy et al., "Bronchiolitis Obliterans Syndrome in Chemical Workers Producing Diacetyl for Food Flavorings," American Journal of Respiratory and Critical Care Medicine. vol. 176 pp. 498-504 (2007).

Warren et al., "Increasing Hyperpolarized Spin Lifetimes Through True Singlet Eigenstates," Science. vol. 323 pp. 1711-1714.

* cited by examiner

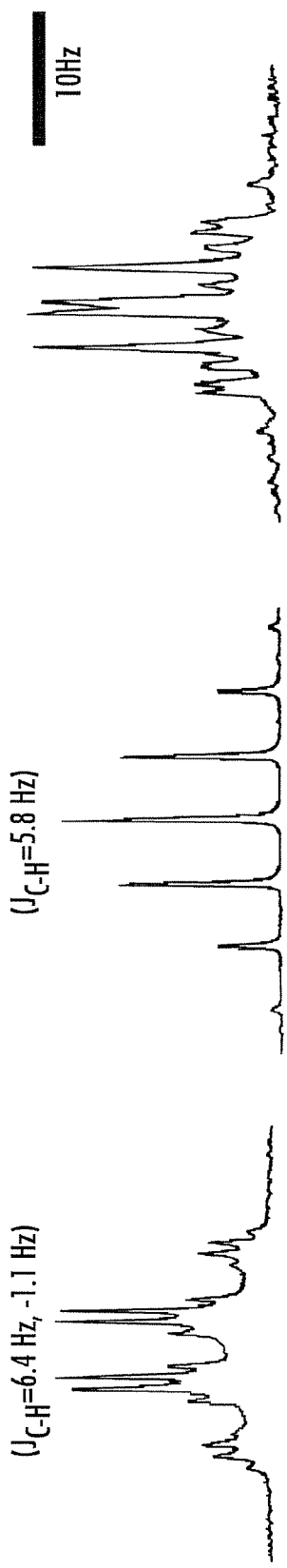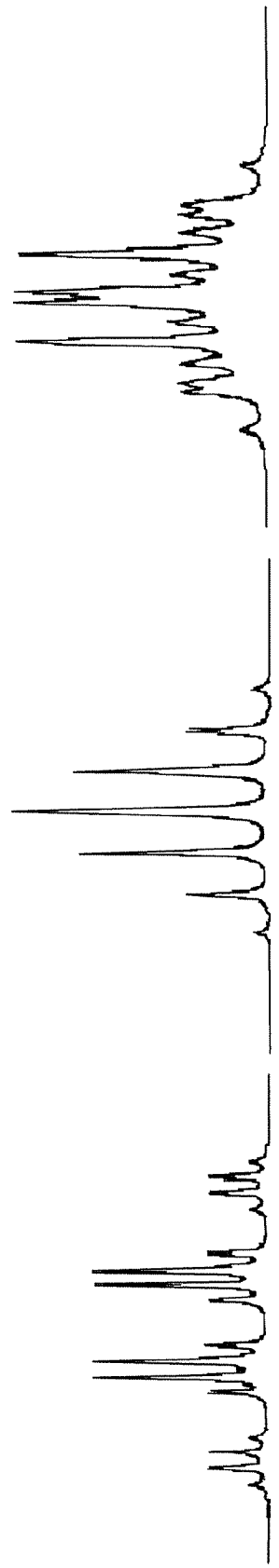

MAGNETIC RESONANCE IMAGING AND/OR SPECTROSCOPY CONTRAST AGENTS AND METHODS OF USE THEREOF

CROSS REFERENCE TO RELATED APPLICATIONS

This application is a national stage of PCT International Application No. PCT/US2009/052393, filed on Jul. 31, 2009, which is based on and claims priority to U.S. Provisional Application Ser. No. 61/085,178, filed Jul. 31, 2008, herein incorporated by reference in its entirety.

GOVERNMENT INTEREST

This presently disclosed subject matter was made with U.S. Government support under Grant No. EB02122 awarded by National Institutes of Health. Thus, the U.S. Government has certain rights in the presently disclosed subject matter.

TECHNICAL FIELD

The presently disclosed subject matter relates to magnetic resonance imaging (MRI) and/or nuclear magnetic resonance (NMR) spectroscopy contrast agents having long effective relaxation times. Also provided are methods of preparing and using the contrast agents.

ABBREVIATIONS $^{13}C$ carbon-13
DNP=dynamic nuclear polarization
FID=free induction decay
HVA=homovanillic acid
Hz=hertz
L-DOPA=L-dihydroxyphenylalanine
MRI=magnetic resonance imaging
ms=millisecond
NMR=nuclear magnetic resonance
PET=positron emission tomography
ppm=parts-per-million
rf=radiofrequency
s=second
t=time
T=Tesla
$T_1$=longitudinal relaxation time constant
$T_2$=spin-spin relaxation time constant
TCA=tricarboxylic acid cycle

BACKGROUND

Nuclear magnetic resonance (NMR), or magnetic resonance spectroscopy, is a powerful, well-established tool for studying chemical samples and sample interactions. In NMR, the spin and magnetism of atomic nuclei are exploited to provide information about the chemical composition, spatial distribution, or molecular motion of molecules or atoms. The imaging analog of NMR, magnetic resonance imaging (MRI), is a powerful technique in biomedical sample imaging.

One of the limitations of NMR and MRI is low intrinsic signal strength. Some attempts to overcome this limitation have involved the use of hyperpolarized contrast agents, which have very large nuclear polarizations and, therefore, sensitivities that are orders of magnitude higher than ordinary molecules. For a few molecules, polarization can persist for 100 or more seconds before the polarized nuclei return to thermal equilibrium. However, for the majority of molecules, including those that could be used as in vivo contrast agents for MRI, polarization lasts more in the range of seconds or tens of seconds.

While such lifetimes can be sufficient for some imaging and/or spectroscopy studies, contrast agents with longer lifetimes are highly desirable to study additional processes of interest, for example processes related to diffusion, flow, slow molecular motion, chemical reactions, metabolism, and drug targeting and distribution, among others. The relaxation of nuclear spins back to thermal equilibrium is characterized by a time constant, $T_1$, known as the longitudinal relaxation time constant or as the spin lattice relaxation time constant. The development of contrast agents having polarization that persists for times longer than $T_1$ would be beneficial for both NMR and MRI.

SUMMARY

The presently disclosed subject matter pertains to a method of providing a contrast agent for magnetic resonance imaging or magnetic resonance spectroscopy, the method comprising:
providing a precursor molecule comprising two J-coupled, non-zero-spin, non-equivalent nuclei, wherein said precursor molecule is chemically convertible to a contrast agent molecule wherein the two J-coupled, non-zero-spin, non-equivalent nuclei are converted to equivalent nuclei;
hyperpolarizing the precursor molecule to provide a hyperpolarized precursor molecule;
applying one or more radiofrequency pulse(s) to the hyperpolarized precursor molecule to create one or both of a non-equilibrium $\alpha\beta$ nuclear spin state population and a non-equilibrium $\beta\alpha$ nuclear spin state population; and
chemically converting the hyperpolarized precursor molecule into a contrast agent molecule by converting the two J-coupled, non-zero-spin, non-equivalent nuclei to two J-coupled, non-zero-spin, equivalent nuclei, wherein the contrast agent molecule comprises a non-equilibrium nuclear singlet spin state population and is chemically convertible to a detection molecule wherein said equivalent nuclei are converted to non-equivalent nuclei.

In some embodiments, the contrast agent molecule is chemically convertible to the detection molecule under physiological conditions. In some embodiments, the contrast agent molecule is converted to the detection molecule via contact with water. In some embodiments, the contrast agent molecule is converted to the detection molecule via an enzymatic reaction.

In some embodiments, the contrast agent molecule is in chemical equilibrium with the hyperpolarized precursor molecule or the detection molecule. In some embodiments, the chemical equilibrium is perturbed to interconvert the contrast agent molecule and the hyperpolarized precursor molecule, the contrast agent molecule and the detection molecule, or both. In some embodiments, the precursor molecule and the detection molecule have the same molecular structure.

In some embodiments, the two J-coupled, non-zero-spin, non-equivalent nuclei of the precursor molecule are selected from the group including, but not limited to, $^1H$, $^{13}C$, $^{15}N$ and $^{31}P$.

In some embodiments, the hyperpolarizing is performed by dynamic nuclear polarization (DNP).

In some embodiments, chemically converting the hyperpolarized precursor molecule into the contrast agent molecule comprises dehydrating the hyperpolarized precursor molecule. In some embodiments, the dehydrating is accelerated or slowed by changing the pH of an aqueous solvent in which the hyperpolarized precursor molecule is dissolved.

In some embodiments, one or both of the precursor molecule and the detection molecule is the monohydrate of diacetyl. In some embodiments, the contrast agent molecule is selected from the group including, but not limited to, diacetyl, oxolin, alendronate, amitryptyline, nortriptyline, succinate, fumarate, maleimide, catechol, naphthalene, naphthoquinone, phenylbutazone, pyridazine, phthalazine, dopamine, L-dihydroxyphenylalanine (L-DOPA) and derivatives thereof.

In some embodiments, the two J-coupled, non-zero-spin, equivalent nuclei of the contrast agent molecule are free of directly bonded hydrogen atoms. In some embodiments, the two J-coupled, non-zero-spin, equivalent nuclei of the contrast agent molecule are directly bonded to hydrogen atoms and are J-coupled to two other, additional equivalent nuclei, wherein the two other, additional equivalent nuclei are free of directly bonded hydrogen atoms, and whereby application of one or more radiofrequency pulse(s) can transfer a spin state population between the two J-coupled, non-zero-spin, equivalent nuclei and the two other, additional equivalent nuclei.

In some embodiments, the method further comprises incorporating the contrast agent molecule into a pharmaceutically acceptable carrier to provide a pharmaceutically acceptable formulation suitable for administration to a subject. In some embodiments, the subject is a mammal. In some embodiments, the method further comprises encapsulating the contrast agent molecule into a biodegradable delivery format that prevents water contact with the contrast agent molecule prior to complete or partial biodegradation of said delivery format.

In some embodiments, the non-equilibrium nuclear singlet spin state population can persist for a time that is substantially greater than $T_1$. In some embodiments, the non-equilibrium nuclear singlet spin state population can persist for a time that is greater than 3 times $T_1$ or greater than 10 times $T_1$. In some embodiments, the non-equilibrium nuclear singlet spin state population can persist for a time that is between about 3 times $T_1$ and about 10 times $T_1$.

In some embodiments, the presently disclosed subject matter provides a method of imaging a target, the method comprising:

providing a contrast agent molecule having a non-equilibrium singlet state nuclear spin population, wherein providing the contrast agent molecule comprises providing a precursor molecule comprising two J-coupled, non-zero-spin, non-equivalent nuclei, wherein said precursor molecule is chemically convertible to a contrast agent molecule wherein the two J-coupled, non-zero-spin, non-equivalent nuclei are converted to equivalent nuclei; hyperpolarizing the precursor molecule to provide a hyperpolarized precursor molecule; applying one or more radiofrequency pulse(s) to the hyperpolarized precursor molecule to create one or both of a non-equilibrium $\alpha\beta$ nuclear spin state population and a non-equilibrium $\beta\alpha$ nuclear spin state population; and chemically converting the hyperpolarized precursor molecule into the contrast agent molecule by converting the two J-coupled, non-zero-spin, non-equivalent nuclei to two J-coupled, non-zero-spin, equivalent nuclei, wherein the contrast agent molecule comprises a non-equilibrium nuclear singlet spin state population and is chemically convertible to a detection molecule wherein the two J-coupled, non-zero-spin equivalent nuclei are converted to non-equivalent nuclei;

contacting the contrast agent molecule with the target;
allowing the contrast agent molecule to be chemically converted into the detection molecule;

generating a nuclear magnetic resonance signal; and
detecting the nuclear magnetic resonance signal, thereby imaging the target.

In some embodiments, the target is one of a cell, a tissue, an organ, and a subject. In some embodiments, the contacting comprises administering a pharmaceutical formulation comprising the contrast agent to a subject. In some embodiments, the subject is a mammal.

In some embodiments, the presently disclosed subject matter provides a contrast agent comprising a contrast agent molecule prepared by the method comprising:

providing a precursor molecule comprising two J-coupled, non-zero-spin, non-equivalent nuclei, wherein said precursor molecule is chemically convertible to a contrast agent molecule wherein the two J-coupled, non-zero-spin, non-equivalent nuclei are converted to equivalent nuclei; hyperpolarizing the precursor molecule to provide a hyperpolarized precursor molecule; applying one or more radiofrequency pulse(s) to the hyperpolarized precursor molecule to create one or both of a non-equilibrium $\alpha\beta$ nuclear spin state population and a non-equilibrium $\beta\alpha$ nuclear spin state population; and chemically converting the hyperpolarized precursor molecule into a contrast agent molecule by converting the two J-coupled, non-zero-spin, non-equivalent nuclei to two J-coupled, non-zero-spin, equivalent nuclei, wherein the contrast agent molecule comprises a non-equilibrium nuclear singlet spin state population and is chemically convertible to a detection molecule wherein said equivalent nuclei are converted to non-equivalent nuclei; wherein said contrast agent can be used to enhance a signal in one of magnetic resonance imaging or magnetic resonance spectroscopy.

In some embodiments, the contrast agent molecule is encapsulated in a biodegradable drug delivery format that prevents water contact with the contrast agent molecule. In some embodiments, the contrast agent molecule is selected from the group including, but not limited to, diacetyl, oxolin, alendronate, amitryptyline, nortriptyline, succinate, fumarate, maleimide, catechol, naphthalene, naphthoquinone, phenylbutazone, pyridazine, phthalazine, dopamine, L-dihydroxyphenylalanine (L-DOPA) and derivatives thereof.

Accordingly, it is an object of the presently disclosed subject matter to provide contrast agents for use in NMR spectroscopy and MRI.

Certain objects of the presently disclosed subject matter having been stated hereinabove, which are addressed in whole or in part by the presently disclosed subject matter, other objects and aspects will become evident as the description proceeds when taken in connection with the accompanying Examples as best described herein below.

BRIEF DESCRIPTION OF THE DRAWINGS

FIG. 4A is a portion of the $^{13}$C nuclear magnetic resonance (NMR) spectrum of 2-$^{13}$C diacetyl showing the carbonyl region. The coupling constant $J_{C-H}$=6.4 Hz, −1.1 Hz.

FIG. 4B is a portion of the $^{13}$C nuclear magnetic resonance (NMR) spectrum of acetone showing the carbonyl region. The coupling constant $J_{C-H}$=5.8 Hz.

FIG. 4C is a portion of the $^{13}$C nuclear magnetic resonance (NMR) spectrum of 2,3-$^{13}$C diacetyl showing the carbonyl region. For reference the bar in the upper right hand corner represents 10 Hz.

FIG. 4D is a portion of a simulated $^{13}$C nuclear magnetic resonance (NMR) spectrum of 1, 2-$^{13}$C diacetyl showing the carbonyl region when the coupling constant $J_{C-C}$ between the two carbons is zero.

FIG. 4E is a portion of a simulated $^{13}$C nuclear magnetic resonance (NMR) spectrum of 1, 2-$^{13}$C diacetyl showing the carbonyl region when the coupling constant $J_{C-C}$ is larger than all of the other couplings.

FIG. 4F is a portion of a simulated $^{13}$C nuclear magnetic resonance (NMR) spectrum of 1, 2-$^{13}$C diacetyl showing the carbonyl region when the coupling constant $J_{C-C}$ is 50 Hz.

DETAILED DESCRIPTION

Figure 1:
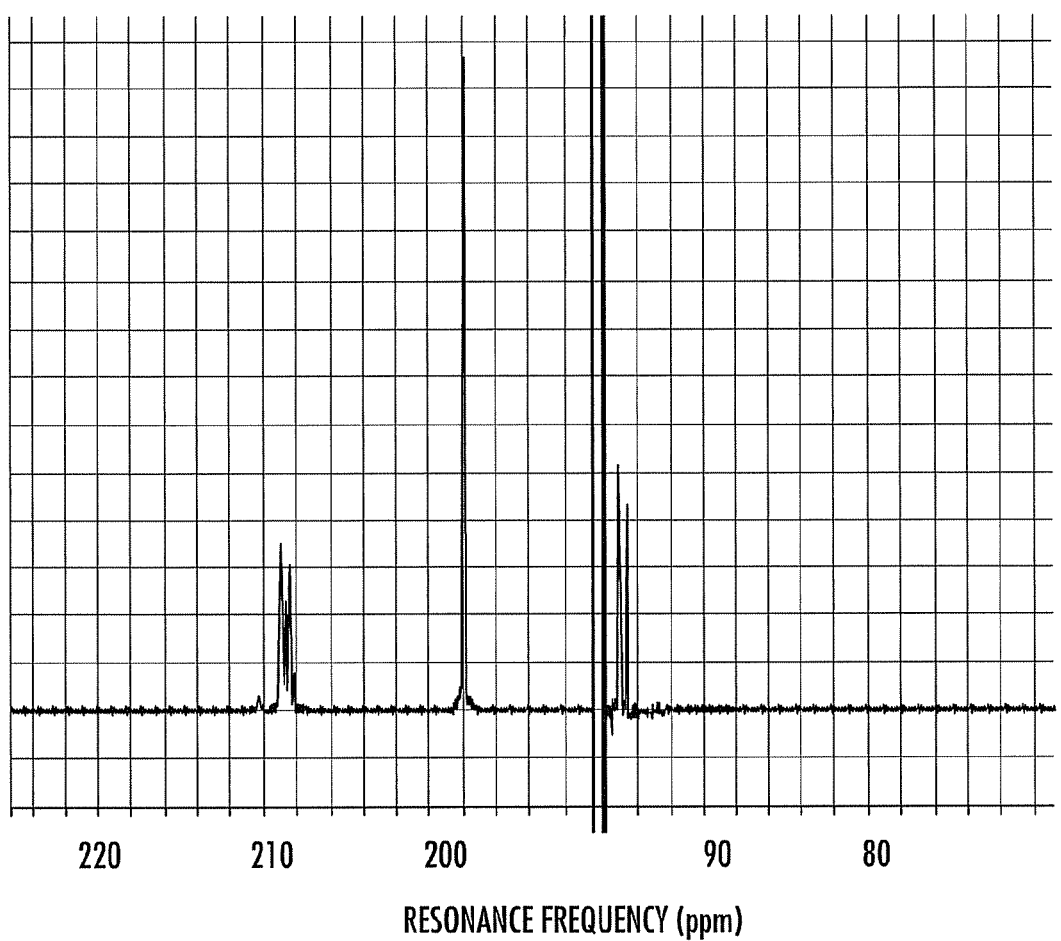
FIG. 1 is a single-shot hyperpolarized $^{13}C$ nuclear magnetic resonance (NMR) spectrum of 2,3-$^{13}C$ diacetyl in water. Hyperpolarized 2,3-$^{13}C$ diacetyl was produced by a commercially available hyperpolarizer (Oxford HYPERSENSE™, Oxford Instruments Molecular Biotools Ltd., Tubney Woods, Abingdon, Oxfordshire, United Kingdom). The sample has about 20% nuclear polarization. The thermally polarized spectrum (not shown) is similar after many averages.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist, unless otherwise noted.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

The term "contrast agent" refers to a contrast agent molecule or a composition comprising a contrast agent molecule that increases the contrast of a tissue, organ, cell or other biological structure being examined, for example using nuclear magnetic resonance imaging (MRI). The contrast agent molecules of the presently disclosed subject matter can also be used to determine the progress of chemical reactions or non-biological phenomena (e.g., chemical diffusion) via nuclear magnetic resonance (NMR) spectroscopy.

The term "J-coupling" can also be referred to as spin-spin coupling or scalar coupling. As used herein, J-coupling can refer to a J coupling which is larger than the reciprocal of the spin-spin relaxation time, $T_2$.

As used herein the term "equivalent nuclei" can refer to nuclei having exactly the same chemical shift. If the chemical shifts are identical because the two nuclei are related by some symmetry element, such as a mirror plane, such nuclei can be referred to as "chemically equivalent." Alternatively, the equivalent nuclei can be "effectively equivalent," wherein, by coincidence or choice of field strength, the resonance frequencies of the nuclei will differ by less than the J coupling between them. For example, in some embodiments, the effectively equivalent nuclei can have a chemical shift difference that is at least three times (or at least five times) smaller than the J coupling between them.

"Non-equivalent nuclei" are generally nuclei wherein one nucleus is bonded to at least one chemical group that is different in structure than the chemical group or groups bonded to the other non-equivalent nuclei. Thus, non-equivalent nuclei have a resonance frequency difference which exceeds the J coupling between them.

The term "derivatives" refers to compounds that differ from a named parent compound by the addition or subtraction of one or more atoms or chemical groups. Thus, the term "derivatives" includes, but is not limited to, compounds wherein one or more hydrogen atom of the parent compound has been replaced by one or more alkyl, aralkyl, aryl, acyl, halo, nitro, cyano, hydroxyl, alkoxyl, aryloxyl, or amino groups. For example, the derivative can be the ester or amide of a parent molecule that includes a carbonyl (i.e., a —C(=O)—), carboxylic acid (i.e., a —C(=O)OH group), amine (i.e., a —NH$_2$ or —NHR group, where R is an alkyl or aryl moiety) or hydroxyl (—OH) group. Other derivatives include ethers of hydroxyl-containing parent molecules and N-alkylated amines of amino-containing parent molecules. In addition, derivatives of the presently disclosed contrast agent molecules are derivatives wherein the derivatization does not change the equivalency of the equivalent nuclei therein. Thus, any derivative of a named contrast agent molecule includes two J-coupled, non-zero-spin, equivalent nuclei.

The terms "chemically converting" and "chemical transformation" refer to chemical and biochemical reactions wherein one or more bonds are formed or broken. In some embodiments, the term chemically converting refers to a non-photo catalyzed reaction.

The term "physiological conditions" refers to biologically relevant pH, temperature, and salt conditions, such as might be present in vivo (i.e., in a living organism) or in vitro (e.g., in a cell, tissue, organ or mixture of biological molecules outside a living organism). Physiological conditions can refer to the presence of an aqueous solvent (e.g., water or saline), which can be buffered or unbuffered by the presence of a buffering agent (e.g., sodium bicarbonate, sodium carbonate, monopotassium phosphate, dipotassium phosphate, sodium citrate, citric acid, sodium acetate, acetic acid, bicine, cacodylate, tris(hydroxymethyl)methylamine (Tris), N-tris(hydroxymethyl)methylglycine (Tricine), 4-2-hydroxyethyl-1-piperazineethanesulfonic acid (HEPES), piperazine-N,N'-bis(2-ethanesulfonic acid) (PIPES), 2-(N-morpholino)ethanesulfonic acid (MES), 3-(N-morpholino)propanesulfonic acid (MOPS), etc). One or more biological molecules (e.g., proteins, peptides, enzymes, nucleic acids, lipids, carbohydrates, or the like) can be present under physiological conditions.

II. General Considerations

Nuclear magnetic resonance (NMR) and the imaging analog, magnetic resonance imaging (MRI), have become extraordinarily important techniques. MRI has become a very powerful clinical imaging modality, for two fundamental reasons. First, the hardware is mature: modern MRI machines routinely give complex sequences of arbitrarily shaped radiofrequency pulses to create precise excitation, and give magnetic field gradient pulses to suppress magnetization or obtain spatial resolution. More importantly, however, the theoretical framework is mature. No other modern spectroscopy has such a strong theoretical basis, which of course is used to understand the structures of molecules as complicated as proteins in solution. This maturity is even more important in MRI: complications associated with imaging in vivo can often be reduced or eliminated by clever pulse sequence design.

However, the maturity of that theoretical framework also implies that the known limitations of MRI are rather fundamental. The Boltzmann distribution implies that the net fractional magnetization is small at room temperature, so in most MRI studies, the signal arises mostly from water. Contrast then arises primarily from parameters that can be traced back to the spin physics explorations of the 1940s and 1950s (the local bulk magnetization $M_o$, the relaxation parameters $T_1$, $T_2$ and $T_2^*$, and local values of diffusion, sometimes in different directions), which often only have very indirect clinical relevance or correlation with metabolism and cell biochemistry. MRI contrast agents generally have limited specificity, and usually need to be present in high concentration to affect the signal.

These limitations have recently been partially surmounted by the ready commercial availability of hyperpolarized reagents, which have very large nuclear polarizations and thus orders of magnitude higher sensitivity than ordinary molecules. Among the recent methods are techniques to create spin polarized $^3$He (see McFall et al., *Radiology*, 200, 553-558 (1996); and Salerno et al., *Eur. J. Radiol.*, 40, 33-44 (2001)), para-$H_2$ addition across double bonds (see Bowers and Weitekamp, *Phys. Rev. Lett.*, 57, 2645-2648 (1986); Bowers and Weitekamp, *J. Am. Chem. Soc.*, 109, 5541-5542 (1987); Natterer and Bargon, *Progr. Magn. Res. Spectrosc.*, 31, 293-315 (1997); Duckett and Sleigh, *Progr. Nucl., Magn. Res. Spectrosc.*, 34, 71-92 (1999); and Golman et al., *Magnetic Resonance in Medicine*, 46, 1-5 (2001)), and dynamic nuclear polarization (DNP). See Abraqam and Goldman, *Rep. Prog., Phys.*, 41, 395-467 (1978); de Boer et al., *Journal of Low Temperature Physics*, 15, 249-267 (1974); de Boer and Niinikoski, *Nuclear Instruments and Methods*, 114, 495-498 (1974); Hall et al., *Science*, 276, 930-931 (1997); Bajaj et al., *Journal of Magnetic Resonance*, 160, 85-90 (2003); Johansson et al., *Magn. Reson. Med.*, 51, 464-472 (2004); and Ardenkjaer-Larsen et al., *Proc. Natl. Acad. Sci.*, USA, 100, 10158-10163 (2003). All of these methods have demonstrated large nuclear magnetization (>10%, as compared to typical thermal magnetization of $10^{-5}$), with the polarization persisting as long as 100 s in some molecules. Many different research groups have been examining potential uses of such hyperpolarized molecules both in vivo and in vitro. See Kurhanewicz et al., *J. Nucl. Med.* 49(3), 341-344 (2008); Golman et al., *Cancer Research*, 66, 10855-10860 (2006); Merritt et al., *Proc. Natl. Acad. Sci.*, USA, 104, 19773-19777 (2007); Day et al., *Mag. Res. Chem.*, 45(12), 1018-1021 (2007); Gabellieri et al., *J. Am. Chem. Soc.*, 130(14), 4598 (2008).

DNP methodology in particular is very versatile, and hundreds of different molecules have been polarized. However, most DNP studies have focused on $^{13}$C in pyruvate, largely because the $T_1$ relaxation time for the C1 position is relatively long (40 s at 14.1 T), so the polarized nuclei can potentially undergo many reactions before the NMR signal returns to thermal equilibrium and becomes undetectable. Generically, carbon-13 $T_1$ values are expected to be tens of seconds for carbons without attached protons, and much shorter with attached protons. While this lifetime permits some important metabolic processes to be studied, it is vastly shorter than the lifetimes associated with other molecular imaging modalities (e.g., $^{18}$F PET) and provides a fundamental limitation to the ultimate generality of the technique.

Previous studies have demonstrated the use of singlet states comprised of non-symmetry related spins to lengthen $T_1$. See Ahuja, et al., *J. Chemical Physics*, 127, 134112 (2007); Carravetta et al., *Physical Review Letters*, 92, 153003 (2004); Carravetta and Levitt, *J. Am. Chem. Soc.*, 126, 6228-6229 (2004); and Carravetta and Levitt, *J. Chem. Physics*, 122, 214505 (2005). In the studies, molecules with broken symmetry (for example, a single carbon-13) are used. The non-symmetry related spins are manipulated to appear to be equivalent by removing frequency differences with multiple spin echoes (which requires excessive radiofrequency power dissipation in vivo) or by lowering the magnetic field so much that the resonance frequencies are essentially the same (which requires removing the sample from the magnet). The signal is then observed by permitting free evolution in a high field. Both approaches give interesting demonstrations of lifetime increases, but neither is practical for MRI. In addition, at the microscopic level, both of these approaches have certain limitations. For example, relaxation is dominated by the local components of the magnetic field fluctuating near the Larmor frequency, and, if two sites are physically inequivalent, these fluctuations are expected to be poorly correlated, even if the resonance frequencies are nearly the same.

PCT International Patent Application Publication No. WO 2005/015253 relates to an approach that involves lowering the field to create a pseudo-singlet state and to reacting an unsaturated symmetric molecule with parahydrogen to provide a quasi-equilibrium nuclear spin ensemble estate. See also, Carravetta et al., *Physical Review Letters*, 92, 153003 (2004); Carravetta and Levitt, *J. Am. Chem. Soc.*, 126, 6228-6229 (2004); and Carravetta and Levitt, *J. Chem. Physics*, 122, 214505 (2005).

III. Contrast Agents and Methods of Preparing Contrast Agents

The presently disclosed subject matter provides novel methods to make certain molecules have vastly longer effective relaxation times, thus facilitating their practical use in clinical and preclinical magnetic resonance imaging. A central concept is that of storing population in a "singlet state", the only antisymmetric spin state created when two magnetically equivalent nuclear spins are present in the same molecule. In such a system, quantum mechanics predicts that the singlet energy level $2^{1/2}(\alpha\beta-\beta\alpha)$ is disconnected from the other three (triplet) energy levels. This has various consequences. For example, the water molecule has two nuclear spins, but a very simple NMR spectrum (i.e., one line) because one of the four possible energy levels is disconnected from all of the others. The singlet state also should have no significant interactions with external magnetic fields, and, thus an extremely long relaxation time, as long as the field does not break the symmetry between the spins. Unfortunately, the signal is also unobservable for the same reasons. The methods of the presently disclosed subject matter take advantage of chemistry to break the symmetry in a controlled way so that signal can be detected. Thus, under certain circumstances, combinations of chemical action and radiofrequency pulses can make these spin states accessible, so that they can be used as a "safe storage" for hyperpolarization.

Prior to the presently disclosed subject matter, most general methods for preparing hyperpolarized reagents do not directly prepare substantial population in singlet states. Further, parahydrogen addition has been demonstrated to work in a very small number of molecules, only one of which at this time has any relevance to biochemistry. The dynamic nuclear polarization method, on the other hand, has been used to hyperpolarize hundreds of different small molecules, for example, via the commercially available Oxford HYPERSENSE™ (Oxford Instruments Molecular Biotools Ltd., Tubney Woods, Abingdon, Oxfordshire, United Kingdom) system. Other methods to hyperpolarize a sample with equivalent carbons, nitrogens, or phosphorus (for example, transfer of polarization from a highly spin polarized gas or reduction of temperature to achieve increased polarization) also tend not to produce singlet population. The presently disclosed methods can be used for preparing substantial excess population, which requires creation of a precursor that is chemically inequivalent; perturbation of a line in the spectrum (or other methods using if pulses on allowed transitions); and then chemical transformation into the singlet. The presently disclosed subject matter further encompasses many examples of classes of chemical reactions that would be capable in vivo of transforming population between singlet and observable signal and is applicable, in some embodiments, to carbon, nitrogen, or phosphorus atoms without attached hydrogens, which are known to have an appreciably longer relaxation time.

In some embodiments, the presently disclosed subject matter provides a hyperpolarized contrast agent molecule. Generically, hyperpolarized contrast agent molecules that can be used in methods of the presently disclosed subject matter satisfy one or more of the following three conditions. First, the contrast agent molecule can have two equivalent nuclei. For example, the molecule can have two nearby equivalent H, C (e.g., $^{13}$C), N (e.g., $^{15}$N), or P (e.g., $^{31}$P) nuclei. Proximity is important because the nuclei need to have a coupling. In solution phase, this coupling would normally be the so-called scalar or J coupling in NMR. The equivalent nuclei will have a resonance frequency difference much less than the scalar coupling (or zero) and much weaker coupling to other spins.

Secondly, there can be a method for preparing excess (or depleted) population in the singlet state. This is possible if the contrast agent molecule has a precursor where the two nuclei are non-equivalent, and if the precursor can be hyperpolarized by a method such as, but not limited to, dynamic nuclear polarization (DNP). Then combinations of radiofrequency pulses can be used to perturb the population in the $\alpha\beta$ and $\beta\alpha$ energy levels in the hyperpolarized precursor to increase or decrease the singlet population. Chemical transformation of the hyperpolarized precursor to a species with equivalent nuclei can then lock population in the singlet. Ideally, this chemical transformation is achievable in a time shorter than the normal $T_1$.

Thirdly, for the contrast agent molecule to give desired contrast, there can be a mechanism (e.g., a biological or chemical pathway) which makes the equivalent nuclei non-equivalent again, thus permitting detection of the hyperpolarization. For example, there might be a biological pathway that involves an enzymatic reaction that transforms the contrast agent molecule into a detection molecule in which the nuclei are non-equivalent. As another example, the contrast agent molecule might be encapsulated in a delivery system which excludes water. At an appropriate time, opening or degrading the capsules causes hydration of the contrast agent molecule and, thus, causes the equivalent nuclei to become non-equivalent (e.g., by breaking the symmetry of the contrast agent molecule). Such a mechanism can be employed, for example, when diacetyl is used as a contrast agent molecule.

Some contrast agent molecules, such as, but not limited to diacetyl, comprise no hydrogens attached directly to the equivalent nuclei. Partitioning between hydrophobic and hydrophilic phases can control the rate of conversion of such contrast agent molecules to detectable molecules. For instance, partitioning in vivo modulates the rate of conversion between diacetyl and its first metabolite, acetoin (i.e., $CH_3C$(=O)CH(OH)CH$_3$), which has inequivalent carbons.

In addition to diacetyl, many other molecular systems can be used as contrast agent molecules. Simple examples include oxolin (an antiviral compound with two equivalent carbons and no attached hydrogens) and FOSAMAX™ (i.e., alendronate, Merck & Co., Inc., Whitehouse Station, N.J., United States of America), which has two equivalent P atoms separated by a single carbon. Derivatives of pyridazine or phthalazine, which have recently been shown to have VEGFR-2 inhibitory activity (see Kisselyov et al., *Chem. Biol. Drug Des.*, 68, 308-313 (2006)), and which can have equivalent nitrogen atoms, can also be used. Also, in some embodiments, deuteration or very weak irradiation can essentially eliminate the coupling to outside nuclei.

As directly bonded H atoms are not needed in the DNP method to create hyperpolarization, isotopic substitution of hydrogen with deuterium is possible and thus additional, more complex, molecular systems can also be used as contrast agent molecules according to the presently disclosed subject matter. These molecules include, but are not limited to, the antidepressant amitryptyline and its primary metabolite nortriptyline, whose seven-member ring gets hydroxylated in the liver (see Oleson and Linnet, *Drug Metabolism and Disposition*, 25, 740-744 (1997)), as well as succinate and fumarate, which become asymmetric as they get converted to malate and oxaloacetate in the tricarboxylic acid (TCA) cycle. Succinate can be prepared directly as the (hydrogen) singlet via parahydrogen addition (see Bhattacharya et al., *J. Mag. Resonance*, 186(1), 150-155 (2007)), but, in the past, has generally been singly carbon-13 labeled, intentionally to break the symmetry. In the 2,3- or 1,2,3,4-labeled compound, the singlet could be transferred by radiofrequency (rf) pulses between H and the 2,3-carbons, or to the 1,4 carbons (which are long lived), then back to the 2,3 carbons to have a detectable coupling. Thus, hyperpolarized succinate is accessible by para-hydrogen addition, as well as the DNP hyperpolarization method.

At moderate fields, such as at about 1 Tesla or at between about 0.5 to about 4.0 Tesla (i.e., the field range of commercial MRI machines), even molecules with not quite chemically equivalent nuclei, such as the 3,4-$^{13}$C versions of L-DOPA or dopamine can be used as contrast agent molecules. The degradation pathways of L-DOPA and dopamine lead to compounds such as homovanillic acid (HVA), which has significant asymmetry.

Thus, the presently disclosed subject matter provides, in some embodiments, a contrast agent comprising a contrast agent molecule that allows for retention or "storage" of hyperpolarization for an extended period of time, for example, so that the contrast agent can be used to detect a number of biologically or chemically relevant events. In some embodiments, the presently disclosed subject matter relates to a method of providing a contrast agent for magnetic resonance imaging or magnetic resonance spectroscopy, the method comprising:

providing a precursor molecule comprising two J-coupled, non-zero-spin, non-equivalent nuclei, wherein said precursor molecule is chemically convertible to a contrast agent molecule wherein the two J-coupled, non-zero-spin, non-equivalent nuclei are converted to equivalent nuclei;

hyperpolarizing the precursor molecule to provide a hyperpolarized precursor molecule (which also comprises the two J-coupled, non-zero-spin, non-equivalent nuclei);

applying one or more radiofrequency pulse(s) to the hyperpolarized precursor molecule to create one or both of a non-equilibrium $\alpha\beta$ nuclear spin state population and a non-equilibrium $\beta\alpha$ nuclear spin state population; and chemically converting the hyperpolarized precursor molecule into a contrast agent molecule by converting the two J-coupled, non-zero-spin, non-equivalent nuclei to two J-coupled, non-zero-spin, equivalent nuclei, wherein the contrast agent molecule comprises a non-equilibrium nuclear singlet spin state population and is chemically convertible to a detection molecule wherein said equivalent nuclei are converted into non-equivalent nuclei. In some embodiments, the presently disclosed subject matter relates to the contrast agent molecule prepared according to the above-described method.

In some embodiments, the contrast agent molecule is chemically convertible to the detection molecule under physiological conditions. Thus, in some embodiments, the contrast agent molecule is converted to the detection molecule via contact with water. In some embodiments, the contrast agent molecule is converted to the detection molecule via an enzymatic reaction. In some cases, conversion between equivalent and inequivalent states can be as simple as a change in pH (e.g., in perdeuterated urea or arginine) or removal of water (as in diacetyl), and such systems can be used as reporters in incapsulated delivery systems.

In some embodiments, the contrast agent molecule is in chemical equilibrium with the hyperpolarized precursor molecule or the detection molecule. In some embodiments, the chemical equilibrium can be perturbed (e.g., changed or manipulated) to interconvert the contrast agent molecule and the hyperpolarized precursor molecule, the contrast agent and the detection molecule, or both. For example, the hyperpolarized precursor molecule and/or the detection molecule can be dehydrated to form the contrast agent molecule. In such an embodiment, the pH of an aqueous solvent in which the hyperpolarized precursor molecule or detection molecule is dissolved can be adjusted to accelerate or slow chemical conversion to the contrast agent molecule.

In some embodiments, the contrast agent molecule is selected from the group including, but not limited to, diacetyl, oxolin, alendronate, amitryptyline, nortriptyline, succinate, fumarate, maleimide, catechol, naphthalene, naphthoquinone, phenylbutazone, pyridazine, phthalazine, dopamine, L-dihydroxyphenylalanine (L-DOPA) and derivatives thereof. In some embodiments, the precursor molecule and the detection molecule can have the same molecular structure. In some embodiments, the contrast agent molecule is diacetyl (i.e., $CH_3C(=O)C(=O)CH_3$) and one or both of the precursor molecule and the detection molecule is the monohydrate of diacetyl (ie., $CH_3CH(OH)C(=O)CH_3$). In some embodiments, both the precursor molecule and the detection molecule are the monohydrate of diacetyl.

In some embodiments, the two J-coupled, non-zero-spin, non-equivalent nuclei of the precursor molecule are selected from the group consisting of $^1H$, $^{13}C$, $^{15}N$ and $^{31}P$. In some embodiments, the nuclei are selected from $^{13}C$ and $^{31}P$. In some embodiments, providing the precursor molecule comprises synthetically doping or labeling a molecule with $^{13}C$, $^1H$, $^{15}N$ or $^{31}P$.

In some embodiments, the hyperpolarizing is performed by DNP. DNP refers to transferring spin polarization from electrons to nuclei. DNP can be performed by doping a material with a free radical. The unpaired electrons in the free radical can be polarized, for example, by exposure to a high magnetic field and low temperature. Irradiation at the electron paramagnetic resonance frequency can then serve to transfer polarization to the nuclei. By "hyperpolarization," it is meant that the sample is polarized to a level over that found at room temperature and 1 Tesla, preferably polarized to a polarization degree in excess of 0.1%, more preferably 1%, even more preferably 10%.

In some embodiments, the two J-coupled, non-zero-spin, equivalent nuclei of the contrast agent molecule are free of directly bonded hydrogen atoms. In some embodiments, the two J-coupled, non-zero-spin, equivalent nuclei of the contrast agent molecule are directly bonded to hydrogen atoms and are J-coupled to two other, additional equivalent nuclei within the molecule, wherein the two other, additional equivalent nuclei are free of directly bonded hydrogen atoms, and whereby application of one or more radiofrequency pulse(s) can transfer a spin state population between the two J-coupled, non-zero-spin, equivalent nuclei and the two other, additional equivalent nuclei.

In some embodiments, such as when the contrast is for use in an in vivo MRI study, the method can further comprise incorporating the contrast agent molecule into a pharmaceutically acceptable carrier to provide a pharmaceutically acceptable formulation suitable for administration to a subject. Administration can be by any suitable means, such as, but not limited to, oral, intraperitoneal or intravenous administration. In some embodiments, the contrast agent can be delivered directly to a target organ or tissue of interest in the subject directly via injection or topical application (e.g., to a wound or surgical incision).

In some embodiments, the subject is a mammal. In some embodiments, the mammal is a human. However, the presently disclosed subject matter also relates to the administration of contrast agents to any vertebrate animal (e.g., dogs, cats, horses, cows, goats, sheep, and the like, including both animals kept on farms and in zoos). Thus, the presently disclosed MRI contrast agents can be used in both medical and veterinary practice. In some embodiments, the term "pharmaceutically acceptable carrier" refers to a carrier that is pharmaceutically acceptable in humans, including water, saline, and aqueous solutions that can comprise other diluents in addition to water, including, but not limited to, ethanol, propylene glycol, glycerin, and the like.

In some embodiments, the contrast agent molecule can be encapsulated into a delivery format or vehicle to protect the contrast agent molecule from one or more conditions in an in vivo environment (e.g., for at least a period of time) or to aid in delivery of the contrast agent molecule to a specific location in a subject (e.g., to a particular organ or to tumor). Thus, the delivery format can include one or more targeting groups (e.g., an antibody, antigen, receptor ligand, enzyme substrate, or the like) that directs the contrast agent to a particular tissue, organ or type of cell (e.g., a cancer or other type of diseased cell) due to the presence of receptors or enzymes present on or nearby the tissue, organ or cell.

In some embodiments, the method comprises encapsulating the contrast agent molecule into a biodegradable delivery format that prevents water contact with the contrast agent molecule prior to complete or partial biodegradation of said delivery format. Therefore, in some embodiments, the rate of biodegradation of the delivery format can be chosen or manipulated to control the rate of conversion of contrast agent molecule to detection molecule. Suitable encapsulation agents include, but are not limited to, various biocompatible, biodegradable polymers such as polyglycolic acid (PGA) and copolymers thereof, polylactic acid (PLA) and copolymers thereof, other polyesters and polyamide esters, polyvinyl esters, and polyanhydrides. In some embodiments, the encapsulation agent is not biodegradable, but can swell in the presence of water to allow conversion of the contrast agent molecule to the detection molecule and/or diffusion of the contrast agent molecule or detection molecule out of the encapsulation agent. In some embodiments, the delivery agent is a liposome. For example, the liposome can have a lipophillic interior to protect the contrast agent molecule from physiological conditions until delivery to a site of interest.

In some embodiments, the non-equilibrium nuclear singlet spin state population can persist for a time that is substantially greater than $T_1$. For example, in some embodiments, the non-equilibrium nuclear singlet spin state population can persist for a time that is greater that about 3 times $T_1$. In some embodiments, the non-equilibrium nuclear singlet spin state population can persist for a time that is greater that about 10 times $T_1$. In some embodiments, the non-equilibrium nuclear singlet spin state population can persist for a time that is between about 3 times $T_1$ and about 10 times $T_1$ (e.g., about 3 times $T_1$, about 4 times $T_1$, about 5 times $T_1$, about 6 times about 7 times $T_1$, about 8 times $T_1$, about 9 times $T_1$ or about 10 times $T_1$).

IV. Imaging Methods

In some embodiments, the presently disclosed subject matter provides a method of imaging a target, the method comprising:
providing a contrast agent molecule having a non-equilibrium singlet state nuclear spin population;
contacting the contrast agent molecule with the target;
allowing the contrast agent molecule to be chemically converted into the detection molecule;
generating a nuclear magnetic resonance signal; and
detecting the nuclear magnetic resonance signal, thereby imaging the target; wherein providing the contrast agent molecule comprises: providing a precursor molecule comprising two J-coupled, non-zero-spin, non-equivalent nuclei, wherein said precursor molecule is chemically convertible to a contrast agent molecule wherein the two J-coupled, non-zero-spin, non-equivalent nuclei are converted to equivalent nuclei; hyperpolarizing the precursor molecule to provide a hyperpolarized precursor molecule; applying one or more radiofrequency pulse(s) to the hyperpolarized precursor molecule to create one or both of a non-equilibrium $\alpha\beta$ nuclear spin state population and a non-equilibrium $\beta\alpha$ nuclear spin state population; and chemically converting the hyperpolarized precursor molecule into the contrast agent molecule by converting the two J-coupled, non-zero-spin, non-equivalent nuclei to two J-coupled, non-zero-spin, equivalent nuclei, wherein the contrast agent molecule comprises a non-equilibrium nuclear singlet spin state population and is chemically convertible to a detection molecule wherein the two J-coupled, non-zero-spin equivalent nuclei are converted to non-equivalent nuclei.

In some embodiments, the target is one of a cell, a tissue, an organ, and a subject. In some embodiments, the contrast agent can be used in an NMR study and the target can be a chemical composition (e.g., a non-biochemical reaction mixture or an environmental sample, such as a water sample from a lake, stream, river, ocean, residential water supply, or industrial site).

In some embodiments, the contacting comprises administering a pharmaceutical formulation comprising the contrast agent to a subject. The subject of the presently disclosed imaging methods can be, in many embodiments, a human subject, although it is to be understood the methods described herein are effective with respect to all vertebrate species, which are intended to be included in the term "subject." The methods described herein are particularly useful in the imaging of warm-blooded vertebrates. Thus, the methods can be used as medical or veterinary diagnostic methods in mammals and birds.

More particularly, provided herein is the nuclear magnetic imaging of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the imaging of birds, including the treatment of those kinds of birds that are endangered, kept in zoos or as pets, as well as fowl, and more particularly domesticated fowl, i.e., poultry, such as turkeys, chickens, ducks, geese, guinea fowl, and the like, as they also are of economical importance to humans. Thus, embodiments of the methods described herein include the imaging of livestock, including, but not limited to, domesticated swine (pigs and hogs), ruminants, horses, poultry, and the like.

In some embodiments, providing the contrast agent molecule further comprises incorporating the contrast agent molecule into a pharmaceutically acceptable carrier. In some embodiments, the term "pharmaceutically acceptable carrier" refers to a carrier that is pharmaceutically acceptable in humans, including water, saline, and aqueous solutions that can comprise other diluents in addition to water, including, but not limited to, ethanol, propylene glycol, glycerin, and the like. In some embodiments, the contrast agent molecule is formulated for oral, intravenous, or interperitoneal administration to the subject. In some embodiments, the contrast agent is formulated for administration directly to a site of interest (e.g., a wound or a tumor site accessible via a surgical incision).

In some embodiments, the contrast agent molecule can be incorporated into a delivery format that effects delivery of the agent to a specific site in vivo (e.g., to a particular type of tissue, organ or cell). In some embodiments, providing the contrast agent molecule further comprises encapsulating the contrast agent molecule into a biodegradable delivery format that prevents water contact with the contrast agent molecule prior to complete or partial biodegradation of said delivery format. Thus, in some embodiments, upon complete or partial degradation of the delivery format, the contrast agent molecule will be converted into the detection molecule.

Suitable encapsulation agents for use in preparing the delivery format include, but are not limited to, various biocompatible, biodegradable polymers such as polyglycolic acid (PGA) and copolymers thereof, polylactic acid (PLA) and copolymers thereof, other polyesters and polyamide esters, polyvinyl esters, and polyanhydrides. In some embodiments, the encapsulation agent is not biodegradable, but can swell in the presence of water to allow conversion of the contrast agent molecule to the detection molecule and/or diffusion of the contrast agent molecule or detection molecule out of the encapsulation agent. In some embodiments, the delivery agent is a liposome. For example, the liposome can have a lipophillic interior to protect the contrast agent molecule from physiological conditions until delivery to a site of interest.

In some embodiments, the contrast agent molecule is selected from the group including, but not limited to, diacetyl, oxolin, alendronate, amitryptyline, nortriptyline, succinate, fumarate, maleimide, catechol, naphthalene, naphthoquinone, phenylbutazone, pyridazine, phthalazine, dopamine, L-dihydroxyphenylalanine (L-DOPA) and derivatives thereof.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

$^{13}$C-Labelled Diacetyl $^{13}$C-labelled diacetyl was prepared from $^{13}C_2$ oxalate, which was reacted with N,N'-dimethylethylenediamine to afford 2,3-$^{13}C_2$-1,4-dimethylpiperazine-2,3-dione in 97% yield. Two equivalents of methyl magnesium bromide were added to the piperazine dione to produce the dimethyl piperazine N,O-acetal. Crude acetal was hydrolyzed with 10% aqueous HCl to yield 2,3-$^{13}C_2$-diacetyl, which was purified by fractional distillation. The carbonyl carbons in diacetyl are magnetically equivalent by symmetry, so at modest resolution (such as that commonly achieved in an imaging system), the spectrum is expected to have only a single line. Neat 2,3-$^{13}$C diacetyl does have a single line carbon-13 NMR spectrum, however the carbon spectrum in water has five lines. See FIG. 1. In water, the monohydrate (i.e., $CH_3$—($^{13}$C=O)($^{13}C(OH)_2$)$CH_3$) with classic AX doublets (splitting $J_{c-c}$=50 Hz) is the majority species. See Bell, *Adv. Phys. Org. Chem.,* 4, 1 (1966); Bell and McDougall, *Trans. Faraday Soc.,* 56, 1281-1285 (1960); and Greenzaid et al., *J. Am. Chem. Soc.,* 89, 749 (1967). The dihydrate is undetectable. Equilibrium can be shifted back to diacetyl by changing solvent, and the rate of interconversion is pH dependent. At pH 7, inversion of the diacetyl alone causes recovery in 8 s, which gives the rate of dehydration. Inversion of all lines causes diacetyl to recover in 22 s.

Example 2

Long-Lived Singlet State of Diacetyl

Preparation of the Singlet State of Diacetyl Requires Perterbation of the αβ and βα populations from their equilibrium 25%. Hyperpolarization does not do this efficiently by itself. For example, 20% nuclear polarization (60% α, 40% (3) would imply an αβ population of 24%, only 1% from equilibrium, wasting most of the potential signal. However, since all the energy levels in the hydrate are accessable, suitable pulse sequences can manipulate the αβ and βα populations. The simplest is inversion of one line in one of the doublets (e.g. αα→αβ), which in this example would interchange the 36% as and 24% αβ populations. Dehydration converts the sum of the αβ and βα populations (in this case, 60%) evenly among the singlet αβ-βα and triplet αβ+βα of diacetyl. The singlet population in this case is 30%, six times farther from equilibrium than is produced by DNP alone. After this dehydration, the population should be locked for a very long time, unless it exchanges back to the hydrate.

Figure 2:
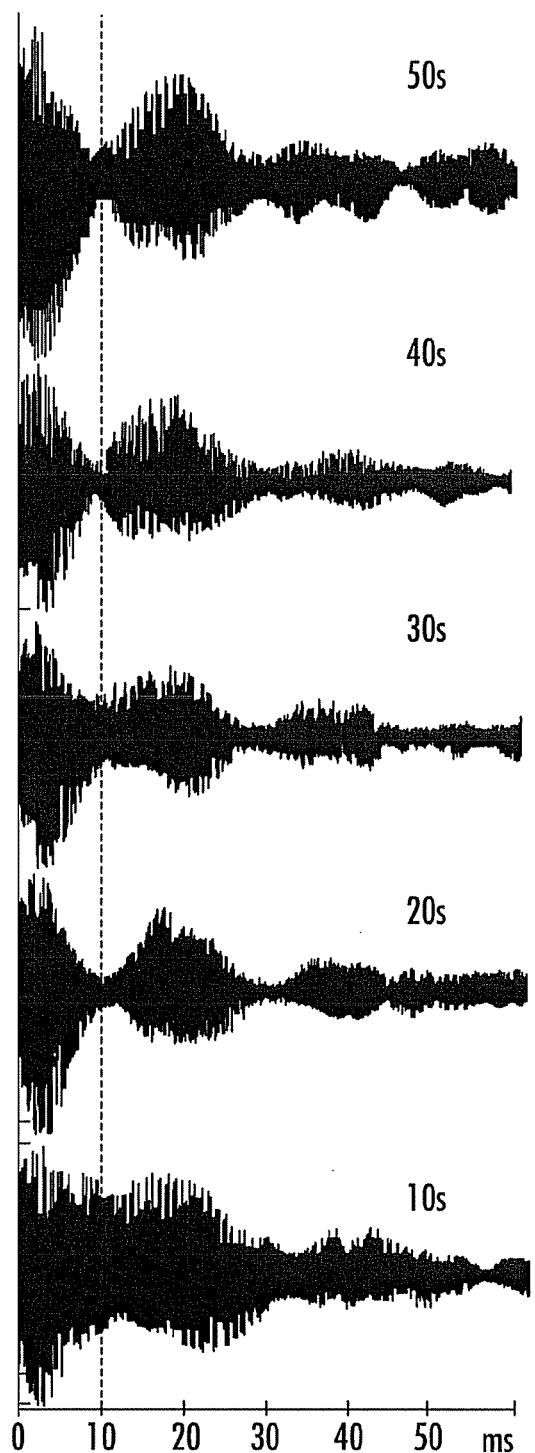
FIG. 2 is a series of free induction decay (FID) signals of the thermally polarized monohydrate of diacetyl after inverting one line, thereby locking the population into a long-lived singlet state. The FIDs should vanish at time=½ J (dotted line).
Figure 3:
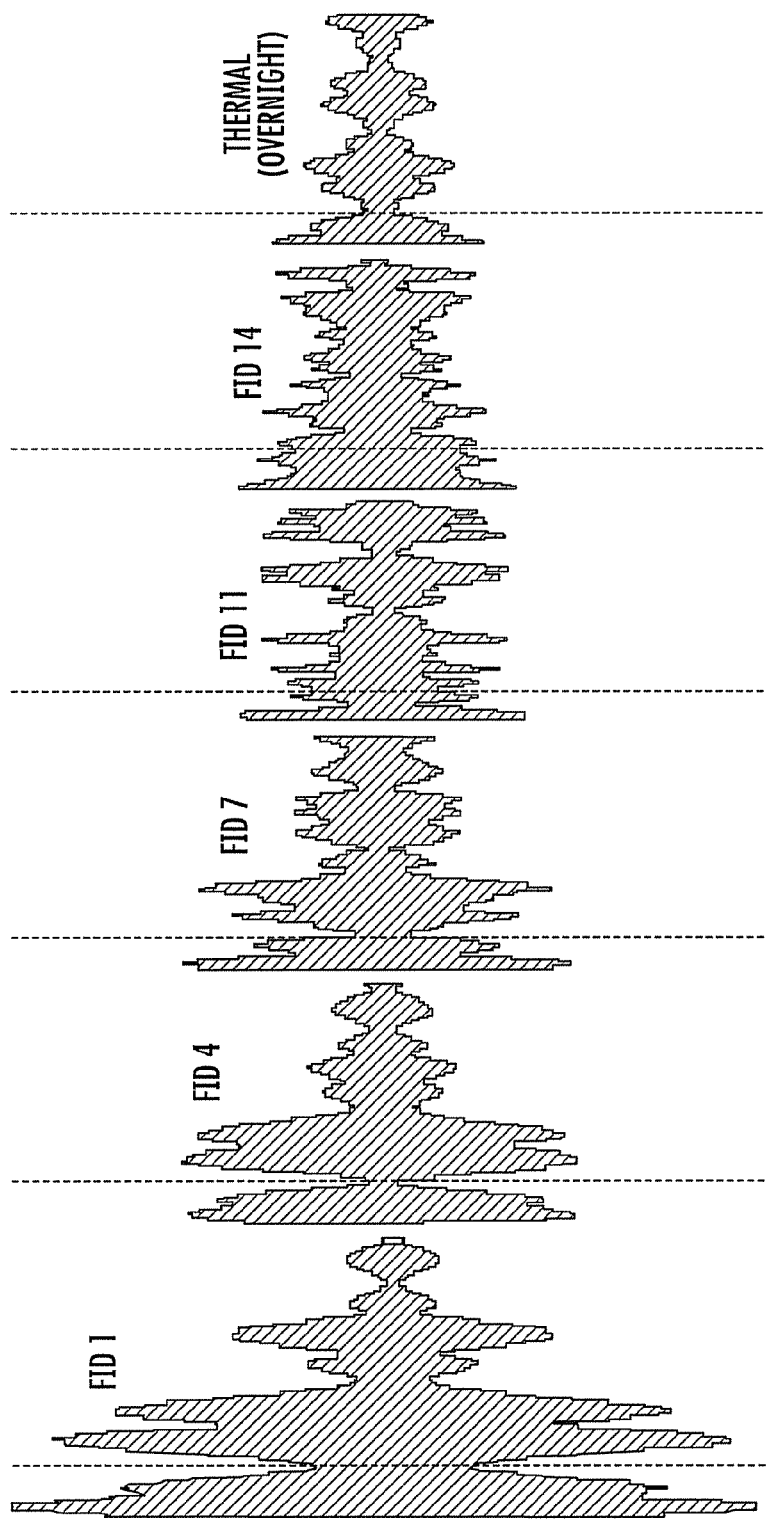
FIG. 3 is a series of free induction decay (FID) signals of the monohydrate of diacetyl in a hyperpolarized diacetyl-water-acetone mixture after inversion of one line.

FIGS. 2 and 3 demonstrate this singlet lifetime extension, both with and without hyperpolarization. FIG. 2 shows the results of inverting only one line in thermally polarized monohydrate of diacetyl, then checking populations later with a small flip angle pulse. Deviations of the an and pa population from equilibrium cause a characteristic alternation of the peak intensities (or, equivalently, FID signal at t=1/(2J)=10 ms, which is absent in the signal from the unperturbed multiplets). FIG. 2 shows that population flows rapidly into diacetyl as expected, but when it returns to the monohydrate (after about 30 s), it has excess αβ and βα population consistent only with a long-lived state (the singlet).

With hyperpolarization, this population could be readily converted back to observable signal in the hydrate (excess population in an and na implies dipolar order, which can be optimally converted to observable signal with a 45° pulse and delay), dramatically extending the effective hyperpolarized lifetime. This differs from most hyperpolarization studies previously reported, where small pulse flip angles are used to conserve the signal for multiple shots. Singlet diacetyl is unaffected by if pulses, so large flip angles do not deplete the stored population. Equilibrium is readily shifted away from the hydrate by the addition of acetone, thus permitting the singlet state to last longer as a spin reservoir. For the data shown in FIG. 3, diacetyl was hyperpolarized in water, then followed inversion of one line of the monohydrate with immediate 3:1 dilution with acetone. See Warren et al., *Science,* 323, 1711-1714 (2009). The individual spectra were acquired by 45° pulses with 10 s time separation. The dynamics are complex (for example, as the equilibrium shifts). Thus, one way to follow what is going on is to look only at the FID from hydrate peaks. See FIG. 3. The first FIDs have excess signal at t=½ J (dotted lines), expected from the selective inversion. At intermediate times (sufficient for dehydration and mixing of the acetone), the FIDs look similar to the thermal ones (averaged over 360 shots). The later FIDs have signal higher than thermal, and the structure is very complex. In the case of FID 14 in FIG. 3, the preceding 45° pulses should have depleted all but 1% of the hyperpolarized signal, the relaxation should have depleted all but 0.1%, so less than $10^{-5}$ should remain in the absence of singlet effects.

Shifting the equilibrium with acetone in vivo is not feasible. However, as diacetyl does not have a dipole moment, it can migrate to the nonpolar phase. For example, it is mostly found in the fatty phase in butter. See Hoecker and Hammer, *J. Dairy Sci.,* 25, 175-185 (1942). Accordingly one application of diacetyl is as a "reporter molecule" in a delivery system, including, but not limited to, functionalized or temperature sensitive liposomes or functionalized ultrasound contrast agents, including those based on encapsulated perfluorocarbons. See Jakobsen, et al., *Eur. Radiol,* 15, 941-945 (2005).

Example 3

Effectively Equivalent Nuclei

In a high resolution spectrometer, the spectra of diacetyl is complicated. See Warren et al., *Science,* 323, 1711-1714

(2009). The carbonyl carbon spins are not strictly fully equivalent. Each carbonyl carbon is coupled differently to the two methyl groups (the C—H couplings are 6.4 Hz and −1.1 Hz). However, the C—C coupling constant (approximately 50 Hz) significantly exceeds these couplings. The effect of this can be seen in FIGS. 4A-4F.

FIG. 4A shows the carbonyl region $^{13}$C NMR spectrum of 2-$^{13}$C diacetyl, where the carbon has two different couplings to three hydrogens each and, thus, becomes a quartet of quartets. FIG. 4B shows the carbonyl region $^{13}$C NMR spectrum of acetone, which is a septet due to the equivalence of the six hydrogens. FIG. 4C shows the complicated carbonyl region of the $^{13}$C NMR spectrum of 2,3-$^{13}$C diacetyl, which suggests that the carbon singlet state is nearly disconnected.

FIGS. 4D-4F show simulations of $^{13}$C NMR spectra of 1,2-$^{13}$C diacetyl which further illustrate the near disconnectedness of the carbon singlet state by varying the coupling $J_{C-C}$ between the two carbons. The simulations were prepared using the WindNMR-Pro program, freeware available from the website of Professor Hans Reich at the University of Wisconsin-Madison. When $J_{C-C}=0$, as shown in FIG. 4D, the doubly labelled and singly labeled spectra (FIG. 4A) are comparable, and inspection of the energy levels shows that the carbon singlet is not an eigenstate. The two different scalar couplings readily connect this state to others with the same overall symmetry, but with $(\alpha\beta+\beta\alpha)$ as the carbon component. However, if $J_{C-C}$ is much larger than all other couplings (see FIG. 4E), the spectrum changes dramatically. It collapses back into a septet, similar to the acetone spectrum, excepting that the splitting is not a real coupling. It is the 2.65 Hz average of the couplings between the near and far methyl groups. This result can be explored by exact calculations, which indicate that the spectrum comes from transitions involving $(\alpha\beta+\beta\alpha)$ as a carbon state, which is delocalized over the two carbons and is coupled equally to each hydrogen. The two carbon spins achieve effective magnetic full equivalence and the $(\alpha\beta+\beta\alpha)$ state is completely disconnected and, thus, long-lived.

Similar spin systems with the same properties, such as but not limited to, the $A_2X_2$ case (e.g., 1,2-dichlorobenzene) have been previously studied. See Pople et al., *Can. J. Chem.*, 35, 1060 (1957); and McConnell et al., *Chem. Phys.*, 23, 1152 (1955). In general, it is known that strong couplings can produce deceptively simple spectra. See Abraham and Bernstein, *Can. J. Chem.*, 39, 216 (1961); Anet, *Can. J. Chem.*, 39, 2262 (1961); Musher and Corey, *Tetrahedron*, 18, 791 (1962); and Becker, *High Resolution NMR: Theory and Chemical Applications* (Academic, San Diego, 2000), page 171-175. In the $A_2X_2$ case, 12 lines associated with the A transitions would be expected, not one. As described previously (see Pople et al., *Can. J. Chem.*, 35, 1060 (1957); and McConnell et al., *Chem. Phys.*, 23, 1152 (1955)), one important parameter is the ratio $(J\pm J')/(J_{A-A}-J_{X-X})$, where J and J' are the two different A-X couplings (the minus sign gives the larger value in cases where the couplings have opposite signs). When this ratio is small, simple perturbation theory analysis shows the worst overlap of a carbon singlet state with a true spin eigenstate to be $\{1-0.25((J-J')/J_{A-A}-J_{X-X}))^2\}$, and $T_1$ lengthening is expected to be on the order of $((JA-A-JX-X)/(J-J'))^2$.

Perturbation theory analysis can be extended to the case of diacetyl. Even though the spectra in FIGS. 4C and 4F are quite complex, assuming the couplings have the same value as in the hydrate shows that the average overlap of the singlet state with an eigenstate is better than 0.97. This can be verified by precise numerical analysis of this eight-spin system, predicting more than an order of magnitude lengthening of the spin lifetime. In effect, the strong coupling between the two carbons quenches communication with other spins. Thus, without being bound to any one theory, it is believed that virtually all the spectral complexity comes from the other three carbon states, and singlet to triplet interconversion is slow. Perdeuteration, which can be readily achieved in this system via keto-enol tautomerization, can dramatically reduce even this limited singlet-triplet mixing and further increase the lifetime.

REFERENCES

All references listed below, as well as all references cited in the instant disclosure, including but not limited to all patents, patent applications and publications thereof, and scientific journal articles, are incorporated herein by reference in their entireties to the extent that they supplement, explain, provide a background for, or teach methodology, techniques, and/or compositions employed herein.

Abragam, A. and Goldman, M., *Rep. Prog. Phys.* 41, 395-467 (1978).

Abraham, R. J., and Bernstein, H. J., *Can. J. Chem.*, 39, 216 (1961).

Ahuja, P., Sarkar, R., Vasos, P. R., Bodenhausen, G., *J. Chem. Physics*, 127, 134112 (2007).

Anet, F. A. L., *Can. J. Chem.*, 39, 2262 (1961).

Ardenkjaer-Larsen, J. H., Fridlund, B., Gram, A., Hansson, G., Hansson, L., Lerche, M. H., Servin, R., Thaning, M., Golman, K., *Proc. Natl. Acad. Sci. U.S.A.*, 100, 10158-10163 (2003).

Bajaj, V. S., Farrar, C. T., Hornstein, M. K., Mastovsky, I., Vieregg, J., Bryant, J., Eléna, B., Kreischer, K. E., Temkin, R. J., Griffin, R. G., *Journal of Magnetic Resonance*, 160, 85-90 (2003).

Becker, E. D., *High Resolution NMR: Theory and Chemical Applications*, (Academic, San Diego, 2000), 171-175.

Bell. R. P., *Adv. Phys. Org. Chem.*, 4, 1 (1966).

Bell, R. P., and McDougall, A. O., *Trans. Faraday Soc.* 56, 1281-1285 (1960).

Bhattacharya, P., et al., *Journal of Magnetic Resonance*, 186 (1), 150-155 (2007).

Bowers, C. R., and Weitekamp, D. P., *Phys. Rev. Lett.*, 57, 2645-2648 (1986).

Bowers, C. R., and Weitekamp, D. P., *J Am. Chem. Soc.*, 109, 5541-5542 (1987).

Carravetta, M., Johannessen, O. G., Levitt, M. H., *Physical Review Letters*, 92, 153003 (2004).

Carravetta, M. and Levitt, M. H., *J. Am. Chem. Soc.*, 126(20), 6228-6229 (2004).

Carravetta, M. and Levitt, M. H., *J. Chem. Physics*, 122, 214505 (2005).

Day, L. J.; Mitchell, J. C.; Snowden, M. J.; Davis, A. L., *Magnetic Resonance in Chemistry* 45(12), 1018-1021 (2007).

de Boer, W., Borghini, M., Morimoto, K., Niinikoski, T. O., Udo, T., *Journal of Low Temperature Physics* 15, 249-267 (1974).

de Boer, W., and Niinikoski, T. O., *Nuclear Instruments and Methods* 114, 495-498 (1974).

Duckett, S. B., and Sleigh, C. J., *Progr. Nucl. Magn. Reson. Spectrosc.*, 34, 71-92 (1999).

Gabellieri, C., Reynolds, S., Lavie, A., Payne, G. S., Leach, M. O., Eykyn, T. R., *J. Am. Chem. Soc.*, 130(14), 4598 (2008).

Golman, K., Ardenkjaer-Larsen, J. H., Petersson, J. S., Mansson, S., Leunbach, I., *Proc. Natl. Acad. ScL U.S.A.*, 100, 10435-10439 (2003).

Golman, K., Axelsson, O., Johannesson, H., Månsson, Olofsson, C., Petersson, J. S., *Magnetic Resonance in Medicine*, 46, 1-5 (2001).

Golman, K., in't Zandt, R., Lerche, M., Pehrson, R., Ardenkjaer-Larsen, J. H., *Cancer Research*, 66, 10855-10860, (2006).

Greenzaid, P., Luz, Z., Samuel, D., *J. Am. Chem. Soc.*, 89, 749 (1967).

Hall, D. A., Maus, D. C., Gerfen, G. J., Inati, S. J., Becerra, L. R., Dahlquist, F. W., Griffin, R. G., *Science*, 276, 930-931 (1997).

Hoecker, W. H., and Hammer, B. W., *J. Dairy Sci.*, 25, 175-185 (1942).

Jakobsen, J. Å., Oyen, R., Thomsen, H. S., Morcos, S. K., *Eur. Radiol.*, 15, 941-945 (2005).

Johansson E., Mansson, S., Wirestam, R., Svensson, J., Petersson, J. S., Golman, K., Stahlberg, F., *Magn. Reson. Med.*, 51, 464-472 (2004).

Kiselyov, A. S., Semenov, V. V., Milligan, D., *Chem. Biol., Drug Des.*, 68, 308-313 (2006).

Kurhanewicz, J., Bok, R., Nelson, S. J., Vigneron, D. B., *J. Nucl. Med.*, 49(3), 341-344 (2008).

MacFall, J. R., Charles, H. C., Black, R. D., Middleton, H., Swartz, J. C., Saam, B., Driehuys, B., Erickson, C., Happer, W., Cates, G. D., Johnson, G. A., Ravin, C. E., *Radiology*, 200, 553-558 (1996).

McConnell, H. M., McLean, A. D., Reilly, C. A., *J. Chem. Phys.*, 23, 1152 (1955).

Merritt, M. E., Harrison, C., Storey, C., Jeffrey, F. M., Sherry, A. D., Malloy, C. R., *Proc. Natl. Acad. Sci. U.S.A.*, 104, 19773-19777 (2007).

Musher, J. I., and Corey, E. J., *Tetrahedron*, 18, 791 (1962).

Natterer, J., and Bargon. J., *Progr. Nucl. Magn. Reson. Spectrosc.*, 31, 293-315, (1997).

Oleson, O. V., and Linnet, K., *Drug Metabolism and Disposition*, 25, 740-744 (1997).

Pople, J. A., Schneider, W. G., Bernstein, H. J., *Can. J. Chem.*, 35, 1060 (1957).

PCT International Patent Publication Number WO 2005/015253.

Salerno, M., Altes, T. A., Mugler 3$^{rd}$, J. P., Nakatsu, M., Hatabu, H., de Lange, E. E., *Eur. J. Radiol.*, 40, 33-44 (2001).

Warren, W. S., Jenista, E. R., and Branca, R. T., *Science*, 323, 1711-1714 (2009). It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of providing a contrast agent for magnetic resonance imaging (MRI) or magnetic resonance spectroscopy, the method comprising:
   providing a precursor molecule comprising two J-coupled, non-zero-spin, non-equivalent nuclei, wherein said precursor molecule is chemically convertible to a contrast agent molecule wherein the two J-coupled, non-zero-spin, non-equivalent nuclei are converted to equivalent nuclei;
   hyperpolarizing the precursor molecule to provide a hyperpolarized precursor molecule;
   applying one or more radiofrequency pulse(s) to the hyperpolarized precursor molecule to create one or both of a non-equilibrium $\alpha\beta$ nuclear spin state population and a non-equilibrium $\beta\alpha$ nuclear spin state population; and
   chemically converting the hyperpolarized precursor molecule into a contrast agent molecule by converting the two J-coupled, non-zero-spin, non-equivalent nuclei to two J-coupled, non-zero-spin, equivalent nuclei, wherein the contrast agent molecule comprises a non-equilibrium nuclear singlet spin state population and is chemically convertible to a detection molecule wherein said equivalent nuclei are converted to non-equivalent nuclei.

2. The method of claim 1, wherein the contrast agent molecule is chemically convertible to the detection molecule under physiological conditions.

3. The method of claim 1, wherein the contrast agent molecule is converted to the detection molecule via contact with water.

4. The method of claim 1, wherein the contrast agent molecule is converted to the detection molecule via an enzymatic reaction.

5. The method of claim 1, wherein the contrast agent molecule is in chemical equilibrium with the precursor molecule or the detection molecule.

6. The method of claim 5, wherein the chemical equilibrium is perturbed to interconvert the contrast agent molecule and the hyperpolarized precursor molecule, the contrast agent molecule and the detection molecule, or both.

7. The method of claim 1, wherein the precursor molecule and the detection molecule have the same molecular structure.

8. The method of claim 1, wherein the two J-coupled, non-zero-spin non-equivalent nuclei of the precursor molecule are selected from the group consisting of $^1$H, $^{13}$C, $^{15}$N and $^{31}$P.

9. The method of claim 1, wherein the hyperpolarizing is performed by dynamic nuclear polarization (DNP).

10. The method of claim 1, wherein chemically converting the hyperpolarized precursor molecule into the contrast agent molecule comprises dehydrating the hyperpolarized precursor molecule.

11. The method of claim 10, wherein the dehydrating is accelerated or slowed by changing the pH of an aqueous solvent in which the hyperpolarized precursor molecule is dissolved.

12. A method of providing a contrast agent for magnetic resonance imaging (MRI) or magnetic resonance spectroscopy, the method comprising:
   providing a precursor molecule comprising two J-coupled, non-zero-spin, non-equivalent nuclei, wherein said precursor molecule is chemically convertible to a contrast agent molecule wherein the two J-coupled, non-zero-spin, non-equivalent nuclei are converted to equivalent nuclei;
   hyperpolarizinq the precursor molecule to provide a hyperpolarized precursor molecule;
   applying one or more radiofrequency pulse(s) to the hyperpolarized precursor molecule to create one or both of a non-equilibrium $\alpha\beta$ nuclear spin state population and a non-equilibrium $\beta\alpha$ nuclear spin state population; and
   chemically converting the hyperpolarized precursor molecule into a contrast agent molecule by converting the two J-coupled, non-zero-spin, non-equivalent nuclei to two J-coupled, non-zero-spin, equivalent nuclei, wherein the contrast agent molecule comprises a non-equilibrium nuclear singlet spin state population and is chemically convertible to a detection molecule wherein said equivalent nuclei are converted to non-equivalent nuclei;

further wherein one or both of the precursor molecule and the detection molecule is the monohydrate of diacetyl.

13. The method of claim 1, wherein the contrast agent molecule is selected from the group consisting of diacetyl, oxolin, alendronate, amitryptyline, nortriptyline, succinate, fumarate, maleimide, catechol, naphthalene, naphthoquinone, phenylbutazone, pyridazine, phthalazine, dopamine, L-dihydroxyphenylalanine (L-DOPA) and derivatives thereof.

14. The method of claim 1, wherein the two J-coupled, non-zero-spin, equivalent nuclei of the contrast agent molecule are free of directly bonded hydrogen atoms.

15. The method of claim 1, wherein the two J-coupled, non-zero-spin, equivalent nuclei of the contrast agent molecule are directly bonded to hydrogen atoms and are J-coupled to two other, additional equivalent nuclei, wherein the two other, additional equivalent nuclei are free of directly bonded hydrogen atoms, and whereby application of one or more radiofrequency pulse(s) can transfer a spin state population between the two J-coupled, non-zero-spin, equivalent nuclei and the two other, additional equivalent nuclei.

16. The method of claim 1, further comprising incorporating the contrast agent molecule into a pharmaceutically acceptable carrier to provide a pharmaceutically acceptable formulation suitable for administration to a subject.

17. The method of claim 16, wherein the subject is a mammal.

18. The method of claim 1, further comprising encapsulating the contrast agent molecule into a biodegradable delivery format that prevents water contact with the contrast agent molecule prior to complete or partial biodegradation of said delivery format.

19. The method of claim 1, wherein the non-equilibrium nuclear singlet spin state population can persist for a time that is substantially greater than $T_1$.

20. The method of claim 19, wherein the non-equilibrium nuclear singlet spin state population can persist for a time that is greater than 3 times $T_1$.

21. The method of claim 20 wherein the non-equilibrium nuclear singlet spin state population can persist for a time that is greater than 10 times $T_1$.

22. The method of claim 19, wherein the non-equilibrium nuclear singlet spin state population can persist for a time that is between about 3 times $T_1$ and about 10 times $T_1$.

23. A method of imaging a target, the method comprising:
providing a contrast agent molecule having a non-equilibrium singlet state nuclear spin population, wherein providing the contrast agent molecule comprises:
providing a precursor molecule comprising two J-coupled, non-zero-spin, non-equivalent nuclei, wherein said precursor molecule is chemically convertible to a contrast agent molecule wherein the two J-coupled, non-zero-spin, non-equivalent nuclei are converted to equivalent nuclei;
hyperpolarizing the precursor molecule to provide a hyperpolarized precursor molecule;
applying one or more radiofrequency pulse(s) to the hyperpolarized precursor molecule to create one or both of a non-equilibrium αβ nuclear spin state population and a non-equilibrium pa nuclear spin state population; and
chemically converting the hyperpolarized precursor molecule into the contrast agent molecule by converting the two J-coupled, non-zero-spin, non-equivalent nuclei to two J-coupled, non-zero-spin, equivalent nuclei, wherein the contrast agent molecule comprises a non-equilibrium nuclear singlet spin state population and is chemically convertible to a detection molecule wherein the two J-coupled, non-zero-spin equivalent nuclei are converted to non-equivalent nuclei;
contacting the contrast agent molecule with the target;
allowing the contrast agent molecule to be chemically converted into the detection molecule;
generating a nuclear magnetic resonance signal; and
detecting the nuclear magnetic resonance signal, thereby imaging the target.

24. The method of claim 23, wherein the target is one of a cell, a tissue, an organ, and a subject.

25. The method of claim 24, wherein the contacting comprises administering a pharmaceutical formulation comprising the contrast agent to a subject.

26. The method of claim 25, wherein the subject is a mammal.

27. The method of claim 23, wherein the two J-coupled, non-zero-spin non-equivalent nuclei of the precursor molecule are selected from the group consisting of $^1H$, $^{13}C$, $^{15}N$ and $^{31}P$.

28. The method of claim 23, wherein the hyperpolarizing is performed by dynamic nuclear polarization (DNP).

29. The method of claim 23, wherein chemically converting the hyperpolarized precursor molecule into the contrast agent molecule comprises dehydrating the hyperpolarized precursor molecule.

30. The method of claim 29, wherein the dehydrating is accelerated or slowed by changing the pH of an aqueous solvent in which the hyperpolarized precursor molecule is dissolved.

31. The method of claim 23, wherein one or both of the precursor molecule and the detection molecule is the monohydrate of diacetyl.

32. The method of claim 23, wherein the contrast agent molecule is selected from the group consisting of diacetyl, oxolin, alendronate, amitryptyline, nortriptyline, succinate, fumarate, maleimide, catechol, naphthalene, naphthoquinone, phenylbutazone, pyridazine, phthalazine, dopamine, L-dihydroxyphenylalanine (L-DOPA) and derivatives thereof.

33. The method of claim 23, wherein the two J-coupled, non-zero-spin equivalent nuclei of the contrast agent molecule are free of directly bonded hydrogen atoms.

34. The method of claim 23, wherein the two J-coupled, non-zero-spin, equivalent nuclei of the contrast agent molecule are directly bonded to hydrogen atoms and J-coupled to two other, additional equivalent nuclei, wherein the two other, additional equivalent nuclei are free of directly bonded hydrogen atoms, and whereby application of one or more radiofrequency pulse(s) can transfer a spin state population between the two J-coupled, non-zero-spin, equivalent nuclei and the two other, additional equivalent nuclei.

35. The method of claim 23, wherein the contrast agent molecule is chemically convertible to the detection molecule under physiological conditions.

36. The method of claim 23, wherein the contrast agent molecule is converted to the detection molecule via contact with water.

37. The method of claim 23, wherein the contrast agent molecule is converted to the detection molecule via an enzymatic reaction.

38. The method of claim 23, wherein the contrast agent molecule is in chemical equilibrium with the hyperpolarized precursor molecule or the detection molecule.

39. The method of claim 38, wherein the chemical equilibrium is perturbed to interconvert the contrast agent molecule and the hyperpolarized precursor molecule, the contrast agent molecule and the detection molecule, or both.

40. The method of claim 23, wherein the precursor molecule and the detection molecule have the same molecular structure.

41. The method of claim 23, wherein providing the contrast agent molecule further comprises incorporating the contrast agent molecule into a pharmaceutically acceptable carrier.

42. The method of claim 23, wherein providing the contrast agent molecule further comprises encapsulating the contrast agent molecule into a biodegradable delivery format that prevents water contact with the contrast agent molecule prior to complete or partial biodegradation of said delivery format.

* * * * *